(12) United States Patent
Lee

(10) Patent No.: US 9,732,302 B2
(45) Date of Patent: Aug. 15, 2017

(54) SYSTEM AND METHOD FOR SEPARATING HIGH VALUE BY-PRODUCTS FROM GRAINS USED FOR ALCOHOL PRODUCTION

(76) Inventor: Chie Ying Lee, Fremont, CA (US)

( * ) Notice: Subject to any disclaimer, the term of this patent is extended or adjusted under 35 U.S.C. 154(b) by 0 days.

(21) Appl. No.: 13/377,353

(22) PCT Filed: Dec. 5, 2011

(86) PCT No.: PCT/US2011/063228
§ 371 (c)(1),
(2), (4) Date: Dec. 9, 2011

(87) PCT Pub. No.: WO2012/075481
PCT Pub. Date: Jun. 7, 2012

(65) Prior Publication Data
US 2013/0236936 A1    Sep. 12, 2013

Related U.S. Application Data

(60) Provisional application No. 61/419,426, filed on Dec. 3, 2010.

(51) Int. Cl.
| | | |
|---|---|---|
| *C11B 1/02* | (2006.01) | |
| *C12F 3/00* | (2006.01) | |
| *C12P 7/06* | (2006.01) | |
| *C12M 1/00* | (2006.01) | |
| *C12M 1/33* | (2006.01) | |
| *A23J 1/12* | (2006.01) | |
| *C11B 1/06* | (2006.01) | |
| *A23K 10/38* | (2016.01) | |
| *A23K 50/10* | (2016.01) | |
| *B01D 21/26* | (2006.01) | |

(52) U.S. Cl.
CPC . *C11B 1/02* (2013.01); *A23J 1/12* (2013.01); *A23K 10/38* (2016.05); *A23K 50/10* (2016.05); *C11B 1/025* (2013.01); *C11B 1/06* (2013.01); *C12F 3/00* (2013.01); *C12M 21/12* (2013.01); *C12M 43/02* (2013.01); *C12M 45/02* (2013.01); *C12M 45/04* (2013.01); *C12M 45/20* (2013.01); *C12M 47/14* (2013.01); *C12P 7/06* (2013.01); *B01D 21/26* (2013.01); *Y02E 50/17* (2013.01); *Y02P 60/873* (2015.11)

(58) Field of Classification Search
None
See application file for complete search history.

(56) References Cited

U.S. PATENT DOCUMENTS

| | | | |
|---|---|---|---|
| 2,282,797 A * | 5/1942 | Musher | 554/2 |
| 3,236,740 A | 2/1966 | Smith et al. | |
| 3,909,288 A | 9/1975 | Powell et al. | |
| 3,939,281 A | 2/1976 | Schwengers | |
| 4,126,707 A * | 11/1978 | Hart | 426/462 |
| 4,181,748 A | 1/1980 | Chwalek et al. | |
| 4,341,713 A | 7/1982 | Stolp et al. | |
| 4,361,651 A | 11/1982 | Keim | |
| 4,501,814 A | 2/1985 | Schoenrock et al. | |
| 6,254,914 B1 | 7/2001 | Singh et al. | |
| 6,648,978 B2 | 11/2003 | Liaw et al. | |
| 6,899,910 B2 | 5/2005 | Johnston et al. | |
| 6,962,722 B2 | 11/2005 | Dawley et al. | |
| 7,297,236 B1 | 11/2007 | Vander Griend | |
| 7,452,425 B1 | 11/2008 | Langhauser | |
| 7,481,890 B2 | 1/2009 | Cheryan | |
| 7,488,390 B2 | 2/2009 | Langhauser | |
| 7,494,675 B2 | 2/2009 | Abbas et al. | |
| 7,524,522 B2 | 4/2009 | DeLine et al. | |
| 7,569,671 B2 | 8/2009 | Cheryan | |
| 7,572,353 B1 | 8/2009 | Vander Griend | |
| 7,572,627 B2 | 8/2009 | Rieke et al. | |
| 7,601,858 B2 | 10/2009 | Cantrell et al. | |
| 7,608,729 B2 | 10/2009 | Winsness et al. | |
| 7,659,098 B2 | 2/2010 | Yamamoto | |
| 7,670,633 B2 | 3/2010 | Srinivasan et al. | |
| 7,820,418 B2 | 10/2010 | Karl et al. | |
| 7,829,680 B1 | 11/2010 | Sander et al. | |
| 7,858,140 B2 | 12/2010 | Paustian et al. | |
| 2003/0232109 A1 | 12/2003 | Dawley et al. | |

(Continued)

OTHER PUBLICATIONS

International Preliminary Report on Patentability issued in corresponding International Application No. PCT/US2011/063228, received on Jun. 24, 2013 (10 pages).

Search Report and Written Opinion issued in International Patent Application No. PCT/US2011/63228, mailed Apr. 3, 2012, 10 pages.

Moreau, Robert A., et al., "The Composition of Crude Corn Oil Recovered after Fermentation via Centrifugation from a Commercial Dry Grind Ethanol Process," J. Am. Oil Chem. Soc., vol. 87, No. 8, pp. 895-902 (Aug. 1, 2010).

(Continued)

*Primary Examiner* — Blaine Lankford
(74) *Attorney, Agent, or Firm* — Wood Herron & Evans LLP

(57) ABSTRACT

Systems and methods are provided for separating high value by-products, such as oil and/or germ, from grains used for alcohol production. In one embodiment, a method for separating by-products from grains used for alcohol production includes, subjecting milled grains to liquefaction to provide a liquefied starch solution including fiber, protein, and germ. The germ is separated from the liquefied starch solution. The separated germ is ground, e.g., to a particle size less than 50 microns, to release oil to provide a germ/oil mixture. Then, prior to fermentation, the oil is separated from the germ/oil mixture to yield an oil by-product. The pH of the germ/oil mixture can be adjusted to about 8 to about 10.5 and/or cell wall breaking enzymes or chemicals may be added to help release oil from the germ. In one example, the oil yield is greater than 1.0 lb/Bu.

7 Claims, 9 Drawing Sheets

(56) References Cited

U.S. PATENT DOCUMENTS

| | | |
|---|---|---|
| 2004/0028775 A1 | 2/2004 | Olsen et al. |
| 2004/0187863 A1 | 9/2004 | Langhauser |
| 2005/0009133 A1 | 1/2005 | Johnston et al. |
| 2005/0089609 A1 | 4/2005 | Angelini et al. |
| 2005/0175734 A1 | 8/2005 | Angelini et al. |
| 2006/0057251 A1 | 3/2006 | Dawley et al. |
| 2007/0014905 A1 | 1/2007 | Chen et al. |
| 2007/0184541 A1 | 8/2007 | Karl et al. |
| 2008/0026101 A1 | 1/2008 | Nickel et al. |
| 2008/0305206 A1 | 12/2008 | Bisgaard-Frantzen et al. |
| 2008/0318291 A1 | 12/2008 | Langhauser |
| 2009/0017164 A1 | 1/2009 | Schisler et al. |
| 2009/0029432 A1 | 1/2009 | Abbas et al. |
| 2009/0130257 A1 | 5/2009 | Abbas et al. |
| 2009/0186136 A1 | 7/2009 | Lindeboom et al. |
| 2009/0269817 A1 | 10/2009 | Lantero |
| 2009/0311397 A1 | 12/2009 | Whalen et al. |
| 2010/0010197 A1 | 1/2010 | Cheryan |
| 2010/0055741 A1 | 3/2010 | Galvez, III et al. |
| 2010/0159071 A1 | 6/2010 | Redford |
| 2010/0166913 A1 | 7/2010 | Stewart |
| 2010/0206780 A1 | 8/2010 | Srinivasan et al. |
| 2010/0260918 A1 | 10/2010 | Wang et al. |
| 2015/0175734 A1 | 6/2015 | Light et al. |

OTHER PUBLICATIONS

European Patent Office, Extended European Search Report, issued in corresponding European Patent Application No. 11844286.2 dated Sep. 7, 2015.

Chinese Patent Office, Office Action issued in corresponding Chinese Patent Application No. 201180065801.0 and English-language translation (Apr. 3, 2014).

Chinese Patent Office, Second Office Action issued in corresponding Chinese Patent Application 2011800658010.0 and English-language translation (Feb. 25, 2015).

Chinese Patent Office, Third Office Action issued in corresponding Chinese Patent Application No. 2011800658010 mailed on Sep. 15, 2015, 7 pages.

Chinese Patent Office, Fourth Office Action in corresponding Chinese Patent Application No. 201180065801.0 mailed on Jun. 3, 2016, 8 pages.

Chinese Patent Office, Decision to Grant issued in corresponding Chinese Patent Application No. 201180065801.0 mailed on Jan. 3, 2017, 2 pages.

European Patent Office, Office Action issued in corresponding European Patent Application No. 11844286.2 mailed on Jan. 24, 2017, 3 pages.

* cited by examiner

SYSTEM AND METHOD FOR SEPARATING HIGH VALUE BY-PRODUCTS FROM GRAINS USED FOR ALCOHOL PRODUCTION

CROSS-REFERENCE TO RELATED APPLICATIONS

The application claims the benefit of U.S. Provisional Application No. 61/419,426, filed Dec. 3, 2010, the disclosure of which is hereby incorporated by reference herein in its entirety.

TECHNICAL FIELD

The present invention relates generally to a system and method for separating by-products from grains used for alcohol production.

BACKGROUND

One alcohol of great interest today is ethanol, which can be produced from virtually any type of grain, but is most often made from corn. Most of the fuel ethanol in the United States is produced from a wet mill process or a dry grind ethanol process. Although virtually any type and quality of grain can be used to produce ethanol, the feedstock for these processes is typically a corn known as "No. 2 Yellow Dent Corn." The "No. 2" refers to a quality of corn having certain characteristics as defined by the National Grain Inspection Association, as is known in the art. "Yellow Dent" refers to a specific type of corn as is known in the art.

The conventional methods for producing various types of alcohol from grain generally follow similar procedures, depending on whether the process is operated wet or dry. Wet mill corn processing plants convert corn grain into several different co-products, such as germ (for oil extraction), gluten feed (high fiber animal feed), gluten meal (high protein animal feed), and starch-based products such as ethanol, high fructose corn syrup, or food and industrial starch. Dry grind ethanol plants convert corn into two products, namely ethanol and distiller's grains with solubles. If sold as wet animal feed, distiller's wet grains with solubles is referred to as DWGS. If dried for animal feed, distiller's dried grains with solubles is referred to as DDGS. In the standard dry grind ethanol process, one bushel of corn yields approximately 8.2 kg (approximately 17 lbs) of DDGS in addition to the approximately 10.5 liters (approximately 2.8 gal) of ethanol. This co-product provides a critical secondary revenue stream that offsets a portion of the overall ethanol production cost.

With respect to the wet mill process, FIG. 1 is a flow diagram of a typical wet mill ethanol production process 10. The process 10 begins with a steeping step 12 in which corn is soaked for 24 to 48 hours in a solution of water and sulfur dioxide in order to soften the kernels for grinding, leach soluble components into the steep water, and loosen the protein matrix with the endosperm. Corn kernels contain mainly starch, fiber, protein, and oil. The mixture of steeped corn and water is then fed to a degermination mill step (first grinding) 14 in which the corn is ground in a manner that tears open the kernels and releases the germ so as to make a heavy density (8.5 to 9.5 Be) slurry of the ground components, primarily a starch slurry. This is followed by a germ separation step 16 that occurs by flotation and use of a hydrocyclone(s) to separate the germ from the rest of the slurry. The germ is the part of the kernel that contains the oil found in corn. The separated germ stream, which contains some portion of the starch, protein, and fiber, goes to germ washing to remove starch and protein, and then to a dryer to produce about 2.7 to 3.2 Lb. (dry basis) of germ per bushel of corn. The dry germ has about 50% oil content on a dry basis.

The remaining slurry, which is now devoid of germ, but containing fiber, gluten (i.e., protein), and starch, is then subjected to a fine grinding step (second grinding) 20 in which there is total disruption of endosperm and release of endosperm components, namely gluten and starch, from the fiber. This is followed by a fiber separation step 22 in which the slurry is passed through a series of screens in order to separate the fiber from starch and gluten, and to wash the fiber clean of gluten and starch. The fiber separation stage 22 typically employs static pressure screens or rotating paddles mounted in a cylindrical screen (Paddle Screens). Even after washing, the fiber from a typical wet grind mill contains 15 to 20% starch. This starch is sold with the fiber as animal feed. The remaining slurry, which is now devoid of fiber, is subjected to a gluten separation step 24 in which centrifugation or hydrocyclones separate starch from the gluten. The gluten stream goes to a vacuum filter and dryer to produce gluten (protein) meal.

The resulting purified starch co-product then undergoes a jet cooking step 26 to start the process of converting the starch to sugar. Jet cooking refers to a cooking process performed at elevated temperatures and pressures, although the specific temperatures and pressures can vary widely. Typically, jet cooking occurs at a temperature of about 120 to 150° C. (about 248 to 302° F.) and a pressure of about 8.4 to 10.5 kg/cm$^2$ (about 120 to 150 lbs/in$^2$), although the temperature can be as low as about 104 to 107° C. (about 220 to 225° F.) when pressures of about 8.4 kg/cm$^2$ (about 120 lbs/in$^2$) are used. This is followed by liquefaction 28, saccharification 30, fermentation 32, yeast recycling 34 and distillation/dehydration 36. Liquefaction occurs as the mixture, or "mash" is held at 90 to 95° C. in order for alpha-amylase to hydrolyze the gelatinized starch into maltodextrins and oligosaccharides (chains of glucose sugar molecules) to produce a liquefied mash or slurry. In the saccharification step 30, the liquefied mash is cooled to about 50° C. and a commercial enzyme known as gluco-amylase is added. The gluco-amylase hydrolyzes the maltodextrins and short-chained oligosaccharides into single glucose sugar molecules to produce a liquefied mash. In the fermentation step 32, a common strain of yeast (*Saccharomyces cerevisae*) is added to metabolize the glucose sugars into ethanol and $CO_2$.

Upon completion, the fermentation mash ("beer") will contain about 17% to 18% ethanol (volume/volume basis), plus soluble and insoluble solids from all the remaining grain components. The solids and some liquid remaining after fermentation go to an evaporation stage where yeast can be recovered as a byproduct. Yeast can optionally be recycled in a yeast recycling step 34. In some instances, the $CO_2$ is recovered and sold as a commodity product. Subsequent to the fermentation step 32 is the distillation and dehydration step 36 in which the beer is pumped into distillation columns where it is boiled to vaporize the ethanol. The ethanol vapor is condensed in the distillation columns, and liquid alcohol (in this instance, ethanol) exits the top of the distillation columns at about 95% purity (190 proof). The 190 proof ethanol then goes through a molecular sieve dehydration column, which removes the remaining residual water from the ethanol, to yield a final product of essentially 100% ethanol (199.5 proof). This anhydrous ethanol is now ready to be used for motor fuel purposes.

No centrifugation step is necessary at the end of the wet mill ethanol production process 10 as the germ, fiber and gluten have already been removed in the previous separation steps 16, 22 and 24. The "stillage" produced after distillation and dehydration 36 in the wet mill process 10 is often referred to as "whole stillage" although it also is technically not the same type of whole stillage produced with the dry grind process described in FIG. 2 below, since no insoluble solids are present. Other wet mill producers may refer to this type of stillage as "thin" stillage.

The wet grind process 10 can produce a high quality starch product for conversion to alcohol, as well as separate streams of germ, fiber and protein, which can be sold as by-products to generate additional revenue streams. However, the overall yields for various by-products can be less than desirable; and the wet grind process is complicated and costly, requiring high capital investment as well as high-energy costs for operation.

Because the capital cost of wet grind mills can be so prohibitive, some alcohol plants prefer to use a simpler dry grind process. FIG. 2 is a flow diagram of a typical dry grind ethanol production process 100. The process 100 begins with a milling step 102 in which dried whole corn kernels are passed through hammer mills in order to grind them into meal or a fine powder. The ground meal is mixed with water to create a slurry, and a commercial enzyme called alpha-amylase is added (not shown). This slurry is then heated to approximately 120° C. for about 0.5 to three (3) minutes in a pressurized jet cooking process 104 in order to gelatinize (solubilize) the starch in the ground meal. It is noted that some processes exclude a jet cooker and instead have a longer hold time of the slurry in a slurry tank at a temperature from about 50° C. to 95° C.

This is followed by a liquefaction step 106 at which point additional alpha-amylase may be added. The stream after this liquefaction step has about 30% dry solids (DS) content with all the components contained in the corn kernels, including sugars, protein, fiber, starch, germ, oil and salts. This is followed by separate saccharification and fermentation steps, 108 and 110, respectively, although in most commercial dry grind ethanol processes, saccharification and fermentation occur simultaneously. This step is referred to in the industry as "Simultaneous Saccharification and Fermentation" (SSF). Both saccharification and SSF can take as long as about 50 to 60 hours. Fermentation converts the sugar to alcohol. Yeast can optionally be recycled in a yeast recycling step 112. Subsequent to the fermentation step 110 is a distillation and dehydration step 114, much like that in the wet mill process, to recover the alcohol.

Finally, a centrifugation step 116 involves centrifuging the residuals produced with the distillation and dehydration step 114, i.e., "whole stillage" in order to separate the insoluble solids ("wet cake") from the liquid ("thin stillage"). The liquid from the centrifuge contains about 8% to 10% DS. The thin stillage enters evaporators in an evaporation step 118 in order to boil away moisture, leaving a thick syrup which contains the soluble (dissolved) solids from the fermentation (25 to 35% dry solids). The concentrated slurry can be sent to a centrifuge to separate the oil from the syrup. The oil can be sold as a separate high value product. The oil yield is normally about 0.5 Lb/Bu of corn with high free fatty acids content. The free fatty acids are created when the oil is held in the fermenter for approximately 50 hours. The free fatty acids content reduces the value of the oil. The de-oil centrifuge only removes less than 50% because the protein and oil make an emulsion, which cannot be satisfactorily separated.

The syrup, which has more than 10% oil, can be mixed with the centrifuged wet cake, and the mixture may be sold to beef and dairy feedlots as Distillers Wet Grain with Solubles (DWGS). Alternatively, the wet cake and concentrated syrup mixture may be dried in a drying step 120 and sold as Distillers Dried Grain with Solubles (DDGS) to dairy and beef feedlots. This DDGS has all the protein and 75% of the oil in corn. But the value of DDGS is low due to the high percentage of fiber, and in some cases the oil is a hindrance to animal digestion.

Because the dry mill process 100 only produces ethanol and low value DDGS, many companies have started to develop a dry fraction process. In this process, corn goes through a pretreatment step, such as steam treatment, then various types of mechanical separation equipment are utilized to separate the dry fractions of the corn, including the fiber, starch, and oil/germ portion. While these separation processes accomplish some separation of the components, the separation is generally incomplete. For example, the fiber portion normally contains more than 30% starch on a dry basis, and the germ contains more than 25% starch and 35% oil content on a dry basis. In addition, less than 30% of the total oil in the corn kernels is recovered with these processes; and the germ and fiber portions must go through purification stages before they can be sold for a reasonable price.

After the dry fractionation, the starch (with protein) goes through another grind step, then liquefaction, fermentation, distillation, and evaporation to produce alcohol and syrup, much the same as in the dry grind process 100. But the alcohol yield normally is as low as 2.3 gal/Bu of corn because of the loss of starch to the germ and fiber portions. In addition, the purification steps mentioned above for the germ and fiber are complicated and costly. Notably, the dry fraction process does not give sharp separation and produces low purity by-products, which complicates the downstream purification steps. Because of the high costs and low yields, these dry fractionation processes have not been generally accepted by the industry.

Other attempts have been made in the dry grinding industry to desirably recover high value by-products, such as oil. However, attempts to separate oil from the "hammer milled" slurry have failed because of the high concentration of solids and because the oil is not released from the solid particles. Some success has been realized with processes recovering oil from the evaporation stages of the dry mill process. However, the yield is relatively low, and the oil must move through the entire process, including fermentation, prior to evaporation. The presence of the oil in these steps of the process can be detrimental to the efficiency of the remaining parts of the process. Attempts have been made to recover the oil directly after fermentation. However, the process of mixing and fermentation emulsifies the oil, and this makes it very difficult to remove. Other attempts have been made to recover oil directly from corn by solvent extraction but the cost, for example, is too high for commercial use.

It would thus be beneficial to provide an improved system and method for separating by-products from grains used for alcohol production that overcomes various aforementioned drawbacks, such as to produce high value by-products with desirable yield.

SUMMARY OF THE INVENTION

The present invention is directed to a system and method for separating by-products from grains used for alcohol production. The system and method can provide for a sharper separation between oil, protein, fiber, and/or starch, and can produce a purer by-product due to various changes along the alcohol production route.

In one embodiment, a method for separating by-products from grains used for alcohol production includes subjecting milled grains used for alcohol production to liquefaction to provide a liquefied starch solution including fiber, protein, and germ. The germ is separated from the liquefied starch solution, then ground, e.g., to a particle size less than 150 microns (or less than 50 microns) to release oil to provide a germ/oil mixture. Prior to fermentation, the oil from the germ/oil mixture is separated to yield an oil by-product. The pH of the germ/oil mixture can be adjusted to about 8 to about 10.5 and/or enzymes added thereto to help release the oil. The germ/oil mixture also can be subjected to a temperature of about 180° F. to about 200° F. In one example, the oil yield is greater than 1.0 lb/Bu.

In another embodiment, a method for separating by-products from grains used for alcohol production includes subjecting milled grains used for alcohol production to liquefaction to provide a liquefied starch solution including fiber, protein, germ, and oil. The germ and oil are individually separated from the liquefied starch solution to yield an oil by-product. Then, the separated germ is ground to release oil to provide a germ/oil mixture. Prior to fermentation, the oil is separated from the germ/oil mixture to yield an oil by-product.

In yet another embodiment, a method for separating by-products from grains used for alcohol production includes subjecting milled grains used for alcohol production to liquefaction to provide a liquefied starch solution including fiber, protein, germ, and oil. The solids including fiber and germ are separated from the liquefied starch solution. Thereafter and prior to fermentation, the oil from the liquefied starch solution is separated to yield an oil by-product.

In another embodiment, a continuous system for separating by-products from grains used for alcohol production includes a milling device that breaks apart the grains used for alcohol production, and a liquefaction apparatus that helps convert starch of the broken apart grains to sugar to provide a liquefied starch solution, which includes fiber, protein, and germ. The system further includes a germ separator that separates the germ from the liquefied starch solution, and a germ grinder that grinds the separated germ to release oil to provide a germ/oil mixture. A germ/oil separator separates the oil from the germ/oil mixture to yield an oil by-product. Thereafter, a fermentor and distiller ferments and distils, respectively, the liquefied starch solution to produce alcohol.

In yet another embodiment, a continuous system for separating by-products from grains used for alcohol production includes a milling device that breaks apart the grains used for alcohol production, and a liquefaction apparatus that helps convert starch of the broken apart grains to sugar to provide a liquefied starch solution, which includes fiber, protein, germ, and oil. The system further includes a separator that individually separates the germ and the oil from the liquefied starch solution to yield an oil by-product, and a germ grinder that grinds the separated germ to release oil to provide a germ/oil mixture. A germ/oil separator separates the oil from the germ to yield an oil by-product. Thereafter, a fermentor and distiller ferments and distils, respectively, a mixture including the separated germ and the liquefied starch solution to produce alcohol.

In still another embodiment, a continuous system for separating by-products from grains used for alcohol production includes a milling device that breaks apart the grains used for alcohol production, and a liquefaction apparatus that helps convert starch of the broken apart grains to sugar to provide a liquefied starch solution, which includes fiber, protein, germ, and oil. The system further includes a solids/liquids separator that separates solids including the fiber and germ from the liquefied starch solution. Thereafter, an oil separator separates the oil from the liquefied starch solution to yield an oil by-product. And thereafter, a fermentor and distiller ferments and distils, respectively, a mixture including the liquefied starch solution including the protein and the solids including the fiber and germ to produce alcohol.

By virtue of the foregoing, there is provided an improved system and method for separating by-products from grains used for alcohol production that can produce high value by-products with desirable yield.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION OF SPECIFIC EMBODIMENTS

Figure 1:
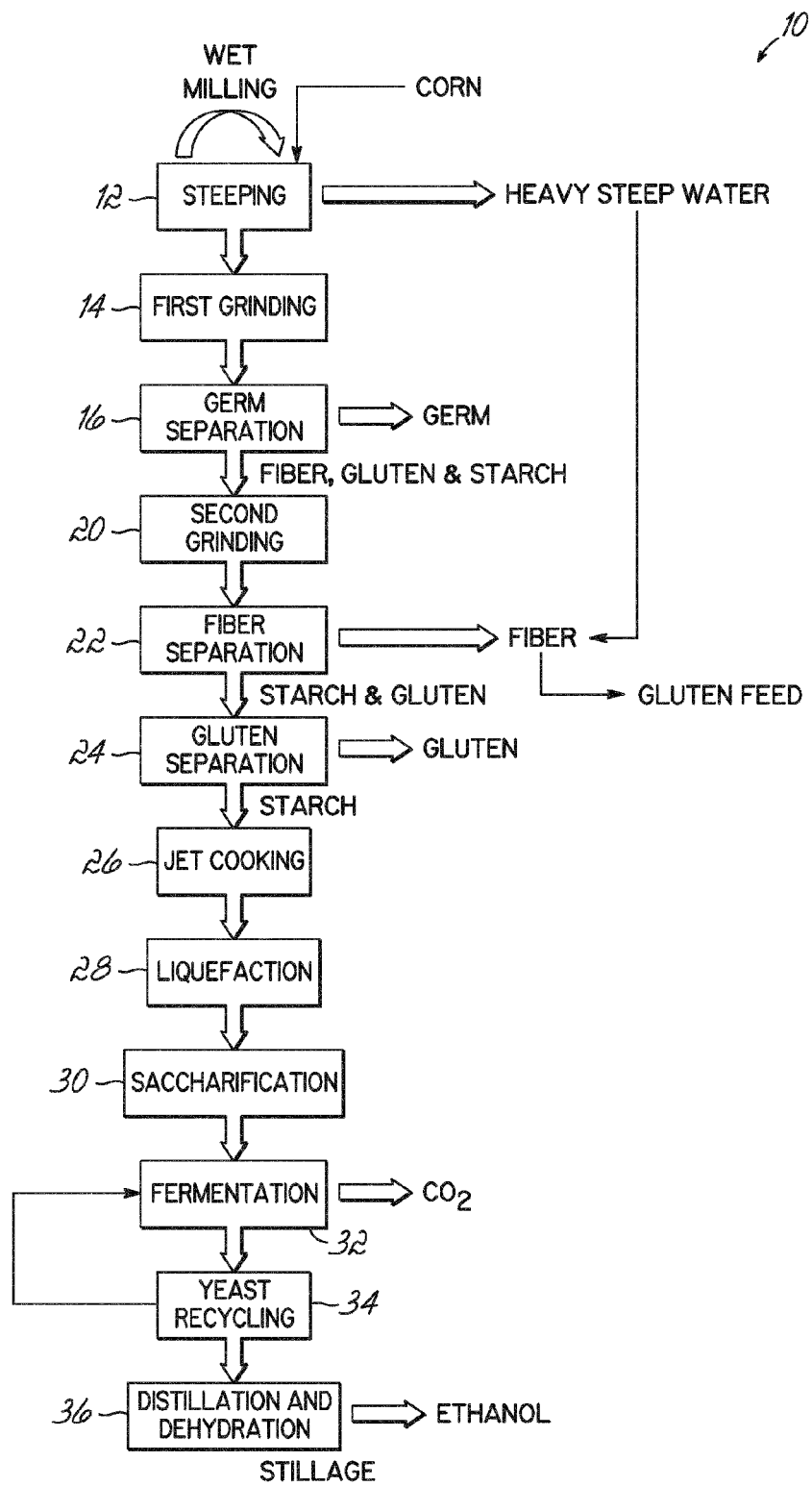
FIG. 1 is a flow diagram of a typical wet mill ethanol production process.
Figure 2:
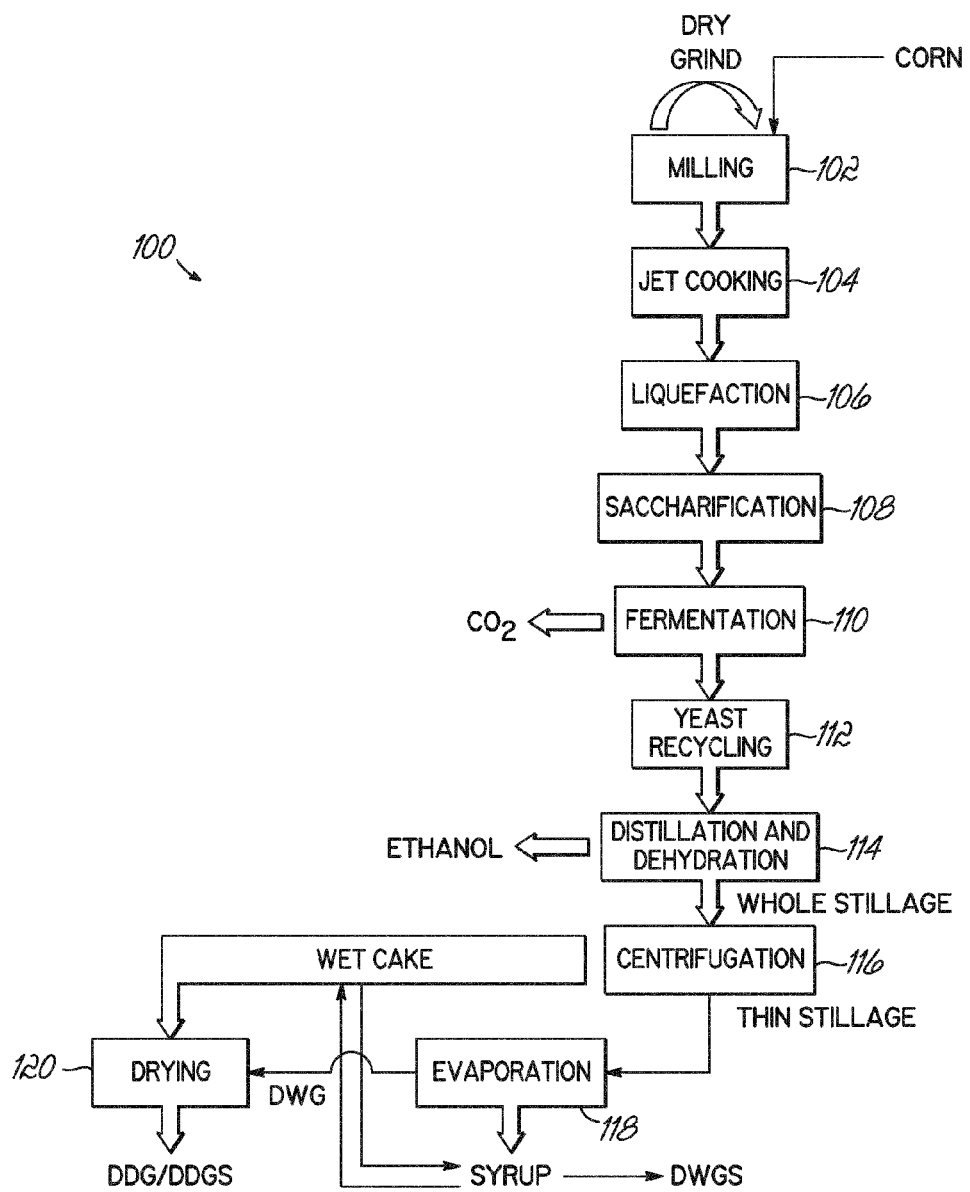
FIG. 2 is a flow diagram of a typical dry mill ethanol production process.

FIGS. 1 and 2 have been discussed above and represent flow diagrams of a typical wet mill and dry grind ethanol production process, respectively.

FIGS. 3-5B illustrate various embodiments of a system and method for separating high value by-products, such as oil, white fiber, and protein meal, from grains used for alcohol production, which are improvements over the typical processes and others. These systems and methods are discussed in detail herein below.

As an overview of the embodiments shown in FIGS. 3-5B, each system and process includes, after milling of the corn and prior to fermentation, separation of germ from a liquefied starch solution utilizing density differences between the different components in that solution. The liquefied starch solution after liquefaction contains oil, germ, grit, protein, and fiber particles with particle sizes ranging from less than 50 micron up to more than 2 mm. The density of oil typically is about 0.9 grams/cc, germ particle is about 1 grams/cc, and the grit, protein and fiber is about 1.1 to 1.15 grams/cc. The liquid solution during soaking/cooking and liquefaction has a density of about 1.05 to 1.12 grams/cc (e.g., about 15 to 28 Brix sugar solution). This heavy density of the liquefied starch solution can be utilized to separate germ and oil from grit, protein, and fiber. In addition, the pH of the slurry at liquefaction is about 5 to 6.

Figure 3:
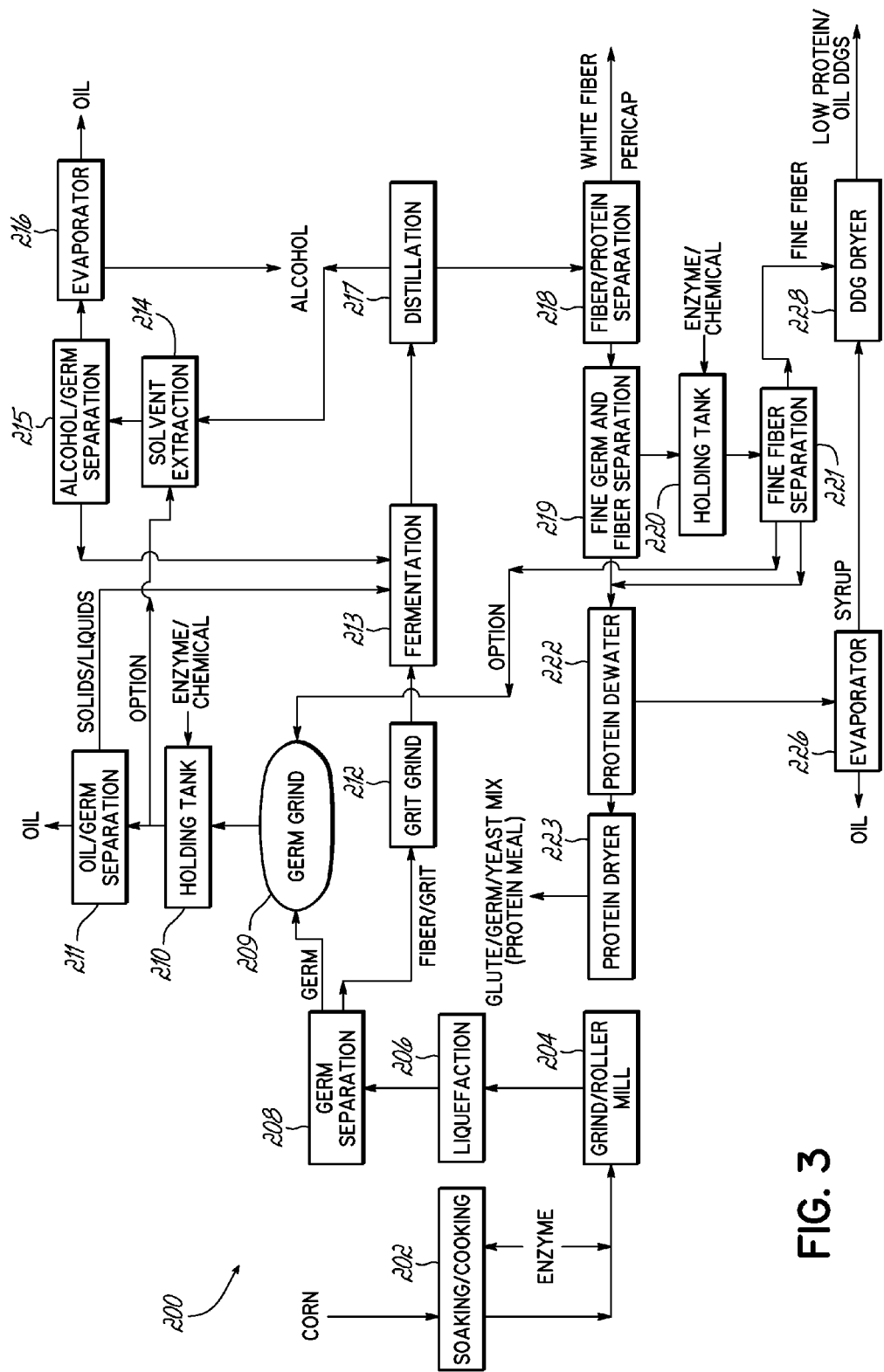
FIG. 3 is a flow diagram of a system and method for separating high value by-products from grains used for alcohol production in accordance with an embodiment of the invention.
Figure 3A:
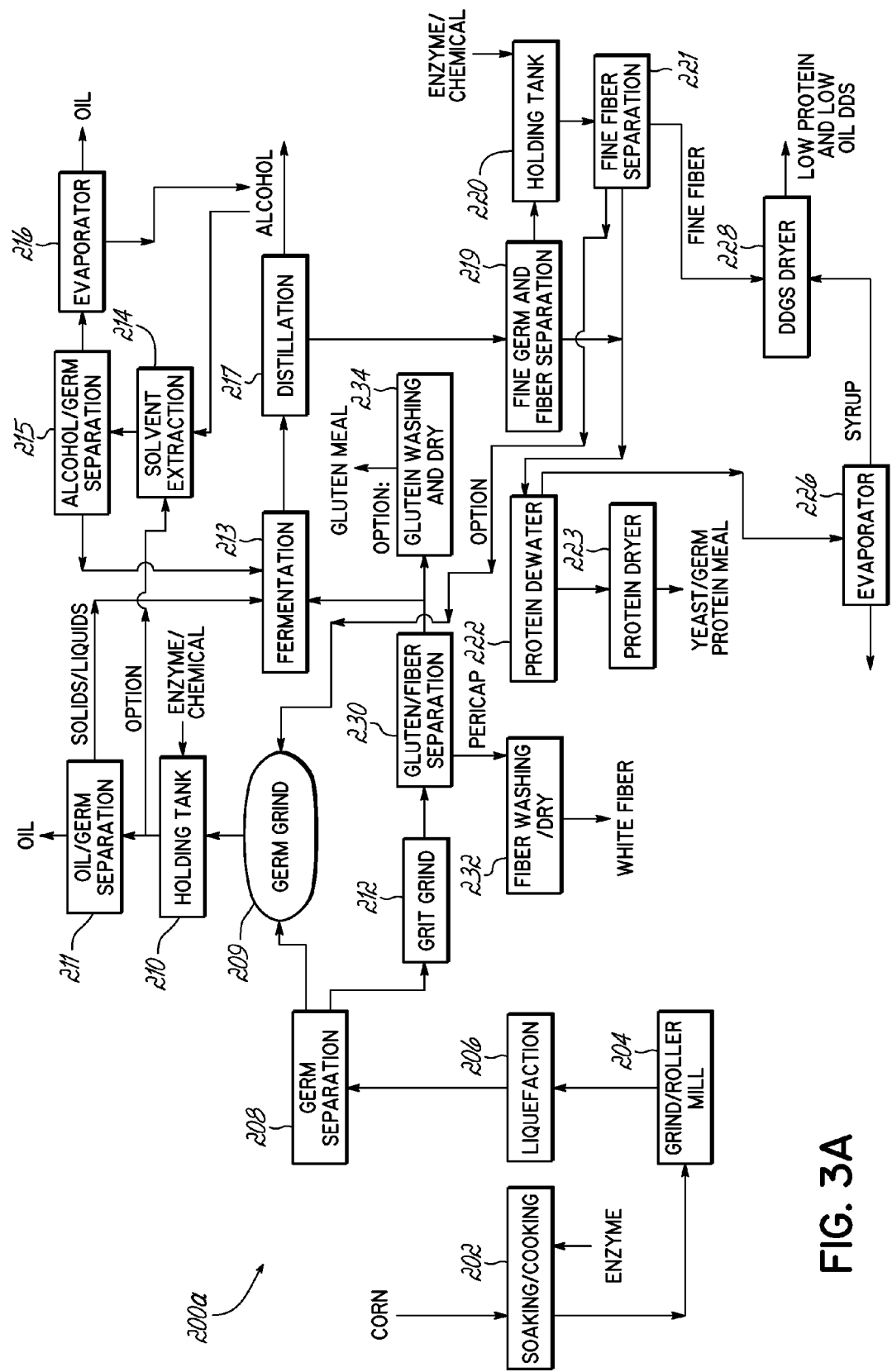
FIG. 3A is a flow diagram of a variation of the system and method of FIG. 3.
Figure 4:
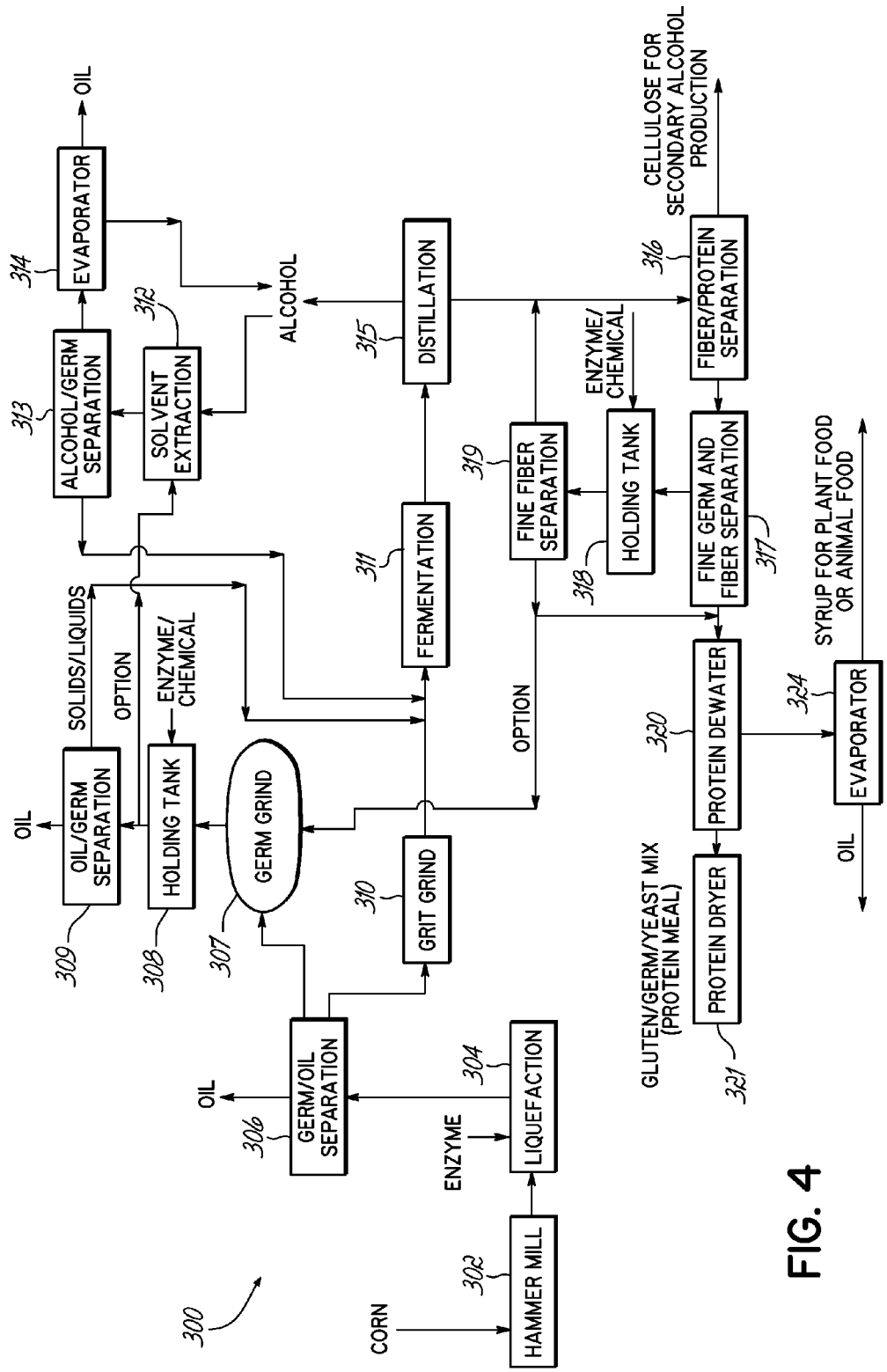
FIG. 4 is a flow diagram of a system and method for separating high value by-products from grains used for alcohol production in accordance with another embodiment of the invention.
Figure 5:
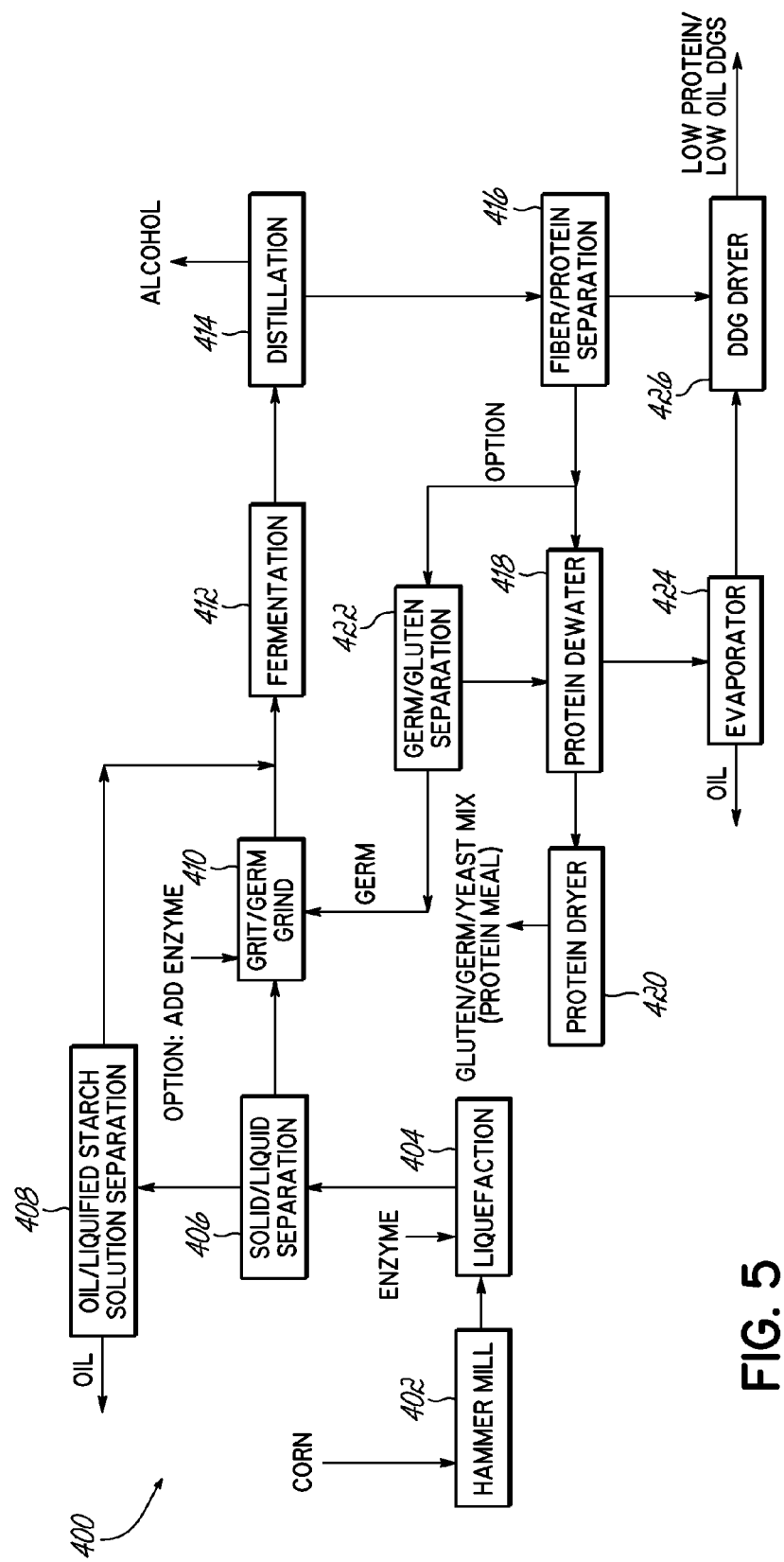
FIG. 5 is a flow diagram of a system and method for separating high value by-products from grains used for alcohol production in accordance with another embodiment of the invention.

There are two general ways to prepare the germ prior to separation from the liquefied starch solution. The first way, as shown in FIGS. 3 and 3A, involves soaking and cooking the corn, then breaking the corn kernel by using a grind or roller mill followed by liquefaction. Alternatively, as shown in FIGS. 4-5B, the soaking and cooking step is eliminated, and much like the current existing dry grind process, the corn can be directly subjected to a hammer mill, for example, followed by liquefaction.

The grinding step is intended to break the germ and grit particles and the bonds between starch and protein, without cutting the fiber too fine. There are three types of fiber: (1) pericarp, with average particle sizes typically about 1 mm to 5 mm; (2) tipcap, with average particle sizes about 500 micron; (3) and fine fiber, with average particle sizes of about 250 micron. A filtration device, such as a fiber centrifuge, can be used to separate the different fiber types by relying on a screen(s) having different sized openings. The pericarp and tipcap are maintained at sizes larger than 300 microns, while the germ and grit are less than that size. Also, fine fiber can create downstream fiber/protein separation problems and can produce a very wet fiber (DDG) cake, which is too costly to dry. An enzyme(s), such as a cell wall degrading enzyme including amylase, protease, or combinations thereof, also can optionally be added during the grind/impact mill step, for example, to help break the bonds between protein, starch, and fiber. During or after soaking/cooking or liquefaction, the liquefied starch solution can go through several possible separation devices, such as a three-phase decanter or cyclone, to separate, for example, germ and oil therefrom, which can be further processed as more specifically discussed below, such as to produce a desirable oil and/or fiber by-product.

With reference now to FIG. 3, a system and method 200, which generally corresponds to a wet type system and process, is shown that separates by-products, such as high value germ and protein, from grains used for alcohol production so as to yield, for example, desirable white fiber (e.g., pericarp) for industrial use and high value oil. In this specific system and method 200, the corn is subjected to a soaking/cooking step 202 whereat the corn is soaked for 4 to 12 hours in soaking tanks filled with water having a temperature around 55° C. to 95° C. An enzyme, such as alpha amylase, may optionally be included in the soaking tanks, as well as about 50 to 100 ppm of sodium sulfite, sulfur dioxide, or the like. The soaked corn then may be subjected to a grinding step 204 using one or more grind mills and/or roller mills to break the corn kernel and release the germ. An enzyme, such as alpha amylase, may optionally be added prior to or to the grinding step 204. Then, the slurry, which includes starch, is subjected to a liquefaction step 206, which provides a liquefied starch solution having a density of about 1.05 to 1.15 grams/cc. At the liquefaction step 206, the starch begins converting to a liquefied starch solution. Any suitable liquefaction apparatus, which is well known in the art, may be utilized here.

Next, the germ is separated at a germ separation step 208 from the liquefied starch solution, as well as from the fiber, protein, and grit, by taking advantage of density differences between the different components in the liquefied starch solution using, for example, a two-stage germ cyclone or a disc or decanter centrifuge designed therefore, in series. In particular, the liquefied starch solution is used as heavy media liquid to float the germ, which is subsequently separated therefrom. The germ is then fed to a grinding device at a grinding step 209 to fine grind the germ particles to a particle size less than 150 microns (or, in another example, less than 50 microns) without creating fine fiber and to release oil from the germ thereby providing an oil/germ mixture.

The ground germ (or oil/germ mixture) is transported to a germ holding tank 210 whereat the pH of the germ in the tank can be adjusted to about 8 to about 10.5 (or about 8 to about 9.5), such as by the addition of chemicals, e.g., sodium hydroxide, lime, sodium carbonate, trisodium phosphate, or the like, to help release oil from the germ. Also, cell wall breaking enzymes, e.g., protease and the like, and/or chemicals, e.g., sodium sulfite and the like, may be added here to help release oil from the germ. In one example, the germ can be held in the tank for about 1 hour at a temperature of about 140° F. to about 200° F. (or about 180° F. to about 200° F.).

The oil and fine germ mixture is next subjected to an oil/germ separation step 211 whereat the oil is separated from the fine germ by taking advantage of density differences between the different components in the residual liquefied starch solution using, for example, a three phase decanter or three phase disc centrifuge. The oil that is recovered at this stage in the process has a much more desirable quality in terms of color and free fatty acid content (from about 2% to about 5%) as compared to oil that is recovered downstream, particularly oil recovered after fermentation. In particular, the color of the pre-fermentation recovered oil is lighter in color and lower in free fatty acid content. The oil yield can include 1.0 lb/Bu or greater. In one example, the oil yield is from about 1.0 to about 1.2 lb/Bu. In addition to, or as an alternative to, the oil recovery efforts prior to fermentation, it also should be understood that similar oil recovery methods may be performed after fermentation.

The underflow liquefied starch solution from the germ separation step 208, which includes fiber, protein, and grit, is subjected to a size reduction step 212 using a grind mill, pin mill, or high pressure cooker, for example, to further breakdown the bond between the fiber, starch, and protein. Although not specifically shown, various enzymes (and types thereof) such as glucoamylase, fungal, cellulose, cellobiose, protease, and the like can be optionally added during the size reduction step 212 and thereafter, including during fermentation, to enhance the separation of components.

The solids, which include the separated fine germ (de-oiled), and residual liquefied starch solution from the oil/germ separation step 211 is joined back up with the liquefied starch solution from the size reduction step 212 at fermentation step 213. The fine germ can be separated out downstream as high value fine germ particle, from the fiber and protein components. In an alternate example, the separated germ that is sent to grind step 209 can be ground to a particle size less than 500 microns but not so small as to release oil from the germ and without creating fine fiber. In one example, the germ particle size is from 50 to 500 micron, with an average size of 250 micron. Thereafter, the fine germ particle can be returned to the liquefied starch solution after the size reduction step 212 and prior to the fermentation step 213 for separating out downstream as high value fine germ particle. In this alternate example, the germ holding tank 210 and oil/germ separation step 211 are removed from the method.

As an alternative, the oil/germ separation step 211 optionally may be replaced by a solvent extraction step 214, alcohol/germ separation step 215, and alcohol evaporation step 216 to recover oil from the oil and fine germ mixture at holding tank 210. In particular, the oil and fine germ mixture may be sent from the holding tank 210 to solvent extraction step 214 whereat recovered alcohol from distillation step 217 is added to the oil and fine germ mixture to extract oil therefrom. The alcohol/oil/germ mixture is then sent to the alcohol/germ separation step 215 to separate the alcohol, which includes the extracted oil, from the fine germ by using, for example, a decanter or disc centrifuge. The solids (or heavy phase), which include the separated fine germ (de-oiled), and residual liquefied starch solution from the alcohol/germ separation step 213 is joined back up with the liquefied starch solution from the size reduction step 212 at fermentation step 213. And the separated alcohol/oil solution (or light phase) is sent to alcohol evaporation step 214 whereat an evaporator separates the oil and alcohol for recovery thereof. A small evaporator can be included as part of the distillation tower. The de-oiled germ normally has about 10% to 20% oil. But with the solvent extraction step 214, the de-oiled germ includes about 4% to 10% oil. The oil yield can include 1.0 lb/Bu or greater. In one example, the oil yield is from about 1.0 to about 1.4 lb/Bu (or from 1.2 to about 1.4 lb/Bu).

At fermentation step 213, the liquefied starch solution, which includes the fiber, protein, grit, and now the fine germ particle, is subjected to fermentation followed by distillation at distillation step 217. The fine germ will partially de-oil during fermentation, which can aid in the later separation and production of a high value oil having reduced or no germ protein. At the distillation tower, the sugars of the liquefied starch solution are separated from the stillage, which includes fiber, protein, and fine germ particles, to produce alcohol.

The fiber can be separated from the fine germ particles, fine fiber, and protein (gluten) at a fiber/protein separation step 218 by differences in particle sizes using a screen device, such as a paddle screen/filtration centrifuge, to remove white fiber, i.e., the pericarp, therefrom. Here, the screen openings normally will be about 1 mm in size, but can range from about 0.3 mm to 1.5 mm. Further concerning particle sizes, the average particle size for protein is about 1 to 5 microns, the fine germ is about 10 to 500 microns, and the various fibers range from about 50 micron to 3 mm size. The separated fiber is washed and dried to produce high value white fiber for industrial use, with a yield of about 2 lb/Bu. The separated fiber can also be used as a feed stock for secondary alcohol production at a yield of about 3 lb/Bu. The white fiber is mainly from pericarp and contains less than 10% protein, less than 2% oil, and less than 2% starch. In one example, the white fiber includes 85% or more pericarp, in another example, 90% or more pericarp, and in another example, 95% or more pericarp.

With continuing reference to FIG. 3, the filtrate from the filtration centrifuge, which includes residual fine fiber and tipcap having sizes of about 30 microns to 300 microns and about 300 microns to 500 microns, as well as fine germ and gluten (protein), moves to a fine germ and fiber separation step 219 whereat fine germ and fine fiber are removed from the gluten solution by a fine screen device, such as paddle screen or pressure screen with a screen size of about 45 micron. The fine germ and fine fiber are transported to a fine germ/fiber holding tank 220 whereat the pH of the fine germ/fiber in the tank can be adjusted to about 8 to about 10.5 (or about 8 to about 9.5), such as by the addition of chemicals, e.g., sodium hydroxide, lime, sodium carbonate, trisodium phosphate, or the like, to help release additional oil from the germ. Also, cell wall breaking enzymes, e.g., protease and the like, and/or chemicals, e.g., sodium sulfite and the like, may be added here to help release additional oil from the germ. The fine germ and fiber mixture is next subjected to a fine fiber separation step 221 whereat the fine fiber is separated from the fine germ by a decanter, for example, and then dried to yield DDG. In one example, the fine fiber includes less than 15% protein and 4% oil.

The centrate from the fine germ and fiber separation step 219 and the centrate from fine fiber separation step 221 is joined back up and goes to a protein recovery/dewatering step 222, which uses, for example, a decanter, a nozzle centrifuge, or a disc decanter to recover the fine germ and protein (as well as spent yeast). Alternatively, the centrate from the fine fiber separation step 221 instead may be optionally dewatered using, for example, a decanter, a nozzle centrifuge, or a disc decanter and sent back to germ grind step 209 to extract more oil. The components from the recovery/dewatering step 222 are sent to a dryer 223 to yield a high value gluten/germ/yeast mix (protein meal) having about 60% gluten and about 40% germ/yeast. The underflow from the protein dewatering step 222 goes to an evaporator 226 to separate oil therefrom and to produce syrup, which can be mixed with the DDG and dried, as represented by numeral 228, to give a low protein (about 20%)/low oil (about 7%) DDGS, such as for cows or pigs. In one example, the protein is no greater than 20% and the oil is no greater than 7%. In another example, sodium sulfite, sulfur dioxide, or the like may be added at any step in the process between the soaking/cooking step 202 and drying step 228. Notably, in this system and method 200, most of the by-product is recovered after fermentation.

With respect to the oil recovery, whenever there is oil recovery, there generally tends to be an emulsion layer formed in the collection tanks. In the tanks where the oil is stored, the oil naturally floats and the emulsion layer sits towards the bottom, along with any solids. There is a significant xanthophyll content in the emulsion layer, and this is good for making chicken egg yolks and skin yellow. With an optional centrifugation step (not shown), the xanthophyll content in the emulsion layer can be recovered and mixed with the protein meal by-product prior to protein drying to increase the feed value. Sodium sulfite, sulfur dioxide, or the like may be added to the wet protein cake, for example, to maintain more than a 20 ppm sulfur dioxide level before the wet protein cake is sent to the protein dryer 223. The sulfur dioxide can prevent the xanthophylls from decomposing inside the protein dryer 223. The oil (light phase) from the centrifuge can go back to the oil storage tank(s).

With reference now to FIG. 3A, this figure depicts a flow diagram of a variation of the system and method 200 of FIG. 3. In this system and method 200a, gluten (protein) meal and white fiber (i.e., pericarp) can be removed prior to fermentation 213. Briefly, by way of background, it is noted that there are 100 to 200 mg/lb of xanthophyll in gluten meal from a typical corn wet mill process. Recovery of the gluten meal before fermentation 213 can cut down on xanthophyll loss during fermentation 213 and subsequent distillation and protein recovery steps 217, 222. In addition, it is noted that the particle size of the pericarp is important for industrial uses, such as those in the paper industry. Larger size pericarp particles, such as from about 1 to about 5 mm, can plug a heat exchanger used during fermentation. So removal of the pericarp before fermentation 213 can avoid these plugging problems and can increase fermentation capacity by about 15% due to the early removal of the pericarp.

As shown in FIG. 3A, after germ separation and the subsequent size reduction step 212, the liquefied starch solution along with the fiber, protein, and grit is subjected to a gluten/fiber separation step 230 using a screen device, such as a filtration centrifuge, to remove white fiber, i.e., the pericarp, therefrom. The screen openings normally will be about 1.5 mm in size, but can range from about 1 mm to about 2 mm. The separated fiber is washed and dried, as represented by numeral 232, to produce high value white fiber for industrial use, with a yield of about 2 lb/Bu. The separated fiber can also be used as a feed stock for secondary alcohol production. For white fiber used as a feedstock for the paper industry, for example, the fiber is mainly from pericarp whereas for secondary alcohol production, the fiber is mainly pericarp, tip cap, and fine fiber, and has a yield of 3 to 4 lb/Bu, and contains less than 14% protein and less than 5% oil. In one example, the white fiber includes 85% or more pericarp, in another example, 90% or more pericarp, and in another example, 95% or more pericarp.

The protein in the liquefied starch solution overflow from the gluten/fiber separation step 230 can optionally be separated out by methods know in the art wherein the gluten moves to a washing and drying step 234 to yield a high value gluten meal having a desirable percentage of xanthopyll, i.e., from about 100 mg/Lb to about 200 mg/Lb. Otherwise, the liquefied starch solution overflow portion meets up with the fine germ particles at the fermentation step 213. The remainder of the process is generally the same as that of FIG. 3, with the exception that the gluten meal and white fiber have been recovered on the front of the process, prior to fermentation 213. In particular, where the white fiber was previously separated from the protein, fine fiber, and fine germ particles and recovered in the system and method 200 of FIG. 3, fine fiber and fine germ having a size larger than 50 microns are separated from residual protein (gluten) at the fine germ and fiber separation step 219 using a fine screen device, such as paddle screen or pressure screen with a screen size of about 45 micron.

The fine germ and fine fiber are then transported to the fine germ/fine fiber holding tank 220 whereat the pH of the fine germ/fiber in the tank can be adjusted to about 8 to about 10.5 (or about 8 to about 9.5), such as by the addition of chemicals, e.g., sodium hydroxide, lime, sodium carbonate, trisodium phosphate, or the like, to help release oil from the germ. Also, cell wall breaking enzymes, e.g., protease and the like, and/or chemicals, e.g., sodium sulfite and the like, may be added here to help release oil from the germ. The germ and fiber mixture is next subjected to fine fiber separation step 221 whereat the fine fiber is separated from the fine germ by a decanter, for example, and then dried to yield DDG. In one example, the fine fiber includes less than 15% protein and 4% oil so as to yield DDG. The centrate from the fine germ and fiber separation step 219 and the centrate from the fine fiber separation step 221 is joined back up and goes to protein recovery/dewatering step 222, which uses, for example, a decanter, a nozzle centrifuge, or a disc decanter to recover the fine germ and residual protein, as well as spent yeast. Alternatively, the centrate from the fine fiber separation step 221 instead may be optionally dewatered using, for example, a decanter, a nozzle centrifuge, or a disc decanter and sent back to germ grind step 209 to extract more oil. The components from the protein recovery/dewatering step 222 are sent to the dryer 223 to yield primarily a germ/yeast mix having about 60% gluten and about 40% germ/yeast.

With reference now to FIG. 4, this figure depicts a flow diagram of another embodiment of a system and method 300 for separating high value by-products from grains used for alcohol production. This system and method 300, which generally corresponds to a dry grind ethanol production system and process, separates various by-products to yield, for example, cellulosic material for secondary alcohol production and high value oil. To that end, in this specific process and method 300, the corn is first subjected to a hammer mill 302, for example, which can be used to grind the corn to particle sizes less than about 7/64 inch and assisting in the release of oil therefrom. In one example, the particle size is from about 50 micron to 3 mm. The grinding helps break up the bonds between the fiber, protein, starch, and germ. In another example, a germ fraction, such as from a dry fraction process, may replace the initially un-ground corn here. The ground corn is mixed with water and sent to a liquefaction step 304, which provides a liquefied starch solution having a density of about 1.05 to 1.15 grams/cc. At the liquefaction step 304, the starch begins converting to a liquefied starch solution. An enzyme(s), such as alpha amylase, can be added to the liquefaction step 304. Any suitable liquefaction apparatus, which is well known in the art, may be utilized here.

The stream from the liquefaction step 304 contains about 1 lb/Bu free oil and about 1.5 lb/Bu germ particle (size ranges from less about 50 micron to about 1 mm), 1 lb/Bu grit (size ranges from about 50 micron to about 1 mm), and 5 lb/Bu fiber (particle size ranges from about 50 micron to about 3 mm). This stream goes to a germ/oil separation step 306, which uses three-phase separation equipment (e.g., a three-phase decanter, a three-phase disc centrifuge, a hydrocyclone, and the like), to individually separate oil and germ from the liquefied starch solution, which includes heavier fiber, protein, and grit, by taking advantage of density differences between the different components in the liquefied starch solution. In particular, the liquefied starch solution is used as heavy media liquid to float the germ and oil, which have densities of about 1.0 to 1.05 grams/cc and 0.9 to 0.92 grams/cc, respectively. It is noted here that if a three-phase disc centrifuge is utilized at germ/oil separation step 306, a pre-screening step (not shown) to remove large sized fiber particles, such as >750 micron, for example, may be required. If this pre-screening step is utilized, the solids portion bypasses the germ/oil step separation step 306 and goes directly to a grinding step 310, which is discussed further below. The oil that is recovered at this stage in the process, i.e., at germ/oil step separation step 306, has a much more desirable quality in terms of color and free fatty acid content (from about 2% to about 5%) as compared to oil that is recovered downstream, particularly oil recovered after fermentation. In particular, the color of the pre-fermentation recovered oil is lighter in color and lower in free fatty acid content. The oil yield can include 1.0 lb/Bu or greater. In one example, the oil yield is from about 1.0 to about 1.2 lb/Bu.

The separated germ is then fed to a grinding device at a grinding step 307 to fine grind the germ particles to a particle size between about 10 to 300 microns to help release additional oil thereby providing an oil/germ mixture. In another example, the particle size is less than 50 microns. The ground germ (or oil/germ mixture) is transported to a germ holding tank 308 whereat the pH of the fine germ can be adjusted to about 8 to about 10.5 (or about 8 to about 9.5), such as by the addition of chemicals, e.g., sodium hydroxide, lime, sodium carbonate, trisodium phosphate, or the like, to help release oil from the germ. Also, cell wall breaking enzymes, e.g., protease and the like, and/or chemicals, e.g., sodium sulfite and the like, may be added here to help release oil from the germ. In one example, the fine germ can be held in the tank for about 1 hour at a temperature of about 140° F. to about 200° F. (or about 180° F. to about 200° F.).

The oil and germ mixture is next subjected to an oil/germ separation step 309 whereat the oil is separated from the germ by taking advantage of density differences between the different components in the residual liquefied starch solution using, for example, a three phase decanter or three phase disc centrifuge. The oil that is recovered at this stage in the process has a much more desirable quality in terms of color and free fatty acid content (from about 2% to about 5%) as compared to oil that is recovered downstream, particularly oil recovered after fermentation. In addition to, or as an alternative to, the oil recovery efforts prior to fermentation, it also should be understood that similar oil recovery methods may be performed after fermentation.

The underflow liquefied starch solution from the germ separation step 306, which includes fiber, protein, and grit, goes through a grinding step 310, such as a grind mill, to further breakdown the bond between the fiber, starch, and protein. Although not specifically shown, various enzymes (and types thereof) such as glucoamylase, fungal, cellulose, cellobiose, protease, and the like can be optionally added during the grind step 310 and thereafter, including during fermentation, to enhance the separation of components.

The solids, which include the separated fine germ, and residual liquefied starch solution from the oil/germ separation step 309 is joined back up with the liquefied starch solution from the size reduction step 310, then subjected to fermentation step 311. The fine germ particle can be separated out downstream as high value fine germ particle (partially de-oiled), from the fiber and protein components. In an alternate example, the separated germ is sent to grinding step 310 and, thereafter, the fine germ particle can be returned to the liquefied starch solution after the size reduction step 310 at fermentation step 311 for separating out downstream as high value fine germ particle. In this alternate example, the germ holding tank 308 and oil/germ separation step 309 are removed from the method.

As an alternative, the oil/germ separation step 309 optionally may be replaced by a solvent extraction step 312, alcohol/germ separation step 313, and alcohol evaporation step 314 to recover oil from the oil and fine germ mixture at holding tank 308. In particular, the oil and fine germ mixture may be sent from the holding tank 308 to solvent extraction step 312 whereat recovered alcohol from distillation step 315 is added to the oil and fine germ mixture to extract oil therefrom. The alcohol/oil/germ mixture is then sent to the alcohol/germ separation step 313 to separate the alcohol, which includes the extracted oil, from the fine germ by using, for example, a decanter or disc centrifuge. The solids (or heavy phase), which include the separated fine germ (de-oiled), and residual liquefied starch solution from the alcohol/germ separation step 313 is joined back up with the liquefied starch solution from the size reduction step 310 at fermentation step 311. And the separated alcohol/oil solution (or light phase) is sent to alcohol evaporation step 314 whereat an evaporator separates the oil and alcohol for recovery thereof. A small evaporator can be included as part of the distillation tower. The de-oiled germ normally has about 10% to 20% oil. But with the solvent extraction step 312, the de-oiled germ includes about 4% to 10% oil. The oil yield can include 1.0 lb/Bu or greater. In one example, the oil yield is from about 1.0 to about 1.4 lb/Bu (or from 1.2 to about 1.4 lb/Bu).

At fermentation step 311, the liquefied starch solution, which includes the fiber, protein, grit, and now the fine germ particle, is subjected to fermentation followed by distillation at distillation step 315. At the distillation tower, the fermented solution (also referred to as beer) is separated from the stillage, which includes fiber, protein, and fine germ particles, to produce alcohol. The fiber can be separated from the fine germ particles and protein (gluten) at a fiber/protein separation step 316 by differences in particle sizes using a screen device, such as a paddle screen, filtration centrifuge, or decanter, to remove the fiber therefrom. The screen openings normally will be about 500 microns to capture amounts of tipcap, pericarp, as well as fine fiber, but can range from about 300 micron to about 700 micron. The separated fiber is washed and optionally dried to produce a cellulose for secondary alcohol production, which is a lower quality fiber than the white fiber produced by the process of FIG. 3, for example. The resulting cellulosic material, which includes pericarp and tipcap (and can include fine fiber) and has less than about 15% protein, less than about 5% oil, and less than about 4% starch, can be sent to a secondary alcohol system, as is known in the art, as feed stock without any further treatment.

With continuing reference to FIG. 4, the centrate from the fiber/protein separation step 316, which includes residual fine fiber and tipcap having sizes of 30 microns to 300 microns and 300 microns to 500 microns, as well as fine germ and gluten, moves to a fine germ and fiber separation step 317 whereat fine germ and fine fiber are removed from the gluten solution by a fine screen device, such as paddle screen or pressure screen with a screen size of about 45 micron. The fine germ and fine fiber are transported to a fine germ/fiber holding tank 318 whereat the pH of the fine germ/fiber in the tank can be adjusted to about 8 to about 10.5 (or about 8 to about 9.5), such as by the addition of chemicals, e.g., sodium hydroxide, lime, sodium carbonate, trisodium phosphate, or the like, to help release additional oil from the germ. Also, cell wall breaking enzymes, e.g., protease and the like, and/or chemicals, e.g., sodium sulfite and the like, may be added here to help release additional oil from the germ. The germ and fiber mixture is next subjected to a fine fiber separation step 319 whereat the fine fiber is separated from the fine germ by a decanter, for example. The fine fiber is recombined with the stillage from distillation so that is may again be subjected to fiber/protein separation step 316.

The centrate from the fine germ and fiber separation step 317 and the overflow from fine fiber separation step 319 is joined back up and goes to a protein recovery/dewatering step 320, which uses, for example, a decanter, a nozzle centrifuge, or a disc decanter to recover the fine germ and protein (as well as spent yeast). Alternatively, the overflow from the fine fiber separation step 319 instead may be optionally dewatered using, for example, a decanter, a nozzle centrifuge, or a disc decanter and sent back to germ grind step 310 to extract more oil. The components from the recovery/dewatering step 320 are sent to a dryer 321 to yield a high value gluten/germ/yeast mix (protein meal) having about 60% gluten and about 40% germ/yeast. The overflow from the protein dewatering step goes to an evaporator 324 to separate any oil therefrom and to produce a high concentrated syrup (more than 65% DS), which can be used, amongst other things, as (a) nutrition for secondary alcohol production, (b) animal feed stock, (c) plant food, (d) and/or anaerobic digestion to produce biogas.

In addition, an optional centrifugation step (not shown) may be provided to recover the xanthophyll content in the emulsion layer of the recovered oils, both prior to and after fermentation 311, and mixed with the protein meal by-product prior to protein drying to increase the feed value. Sodium sulfite, sulfur dioxide, or the like may be added to the wet protein cake, for example, to maintain more than a 20 ppm sulfur dioxide level before the wet protein cake is sent to the protein dryer 321. The sulfur dioxide can prevent the xanthophylls from decomposing inside the protein dryer 321. The overflow from the centrifuge(s) can go back to the oil storage tanks.

Figure 4A:
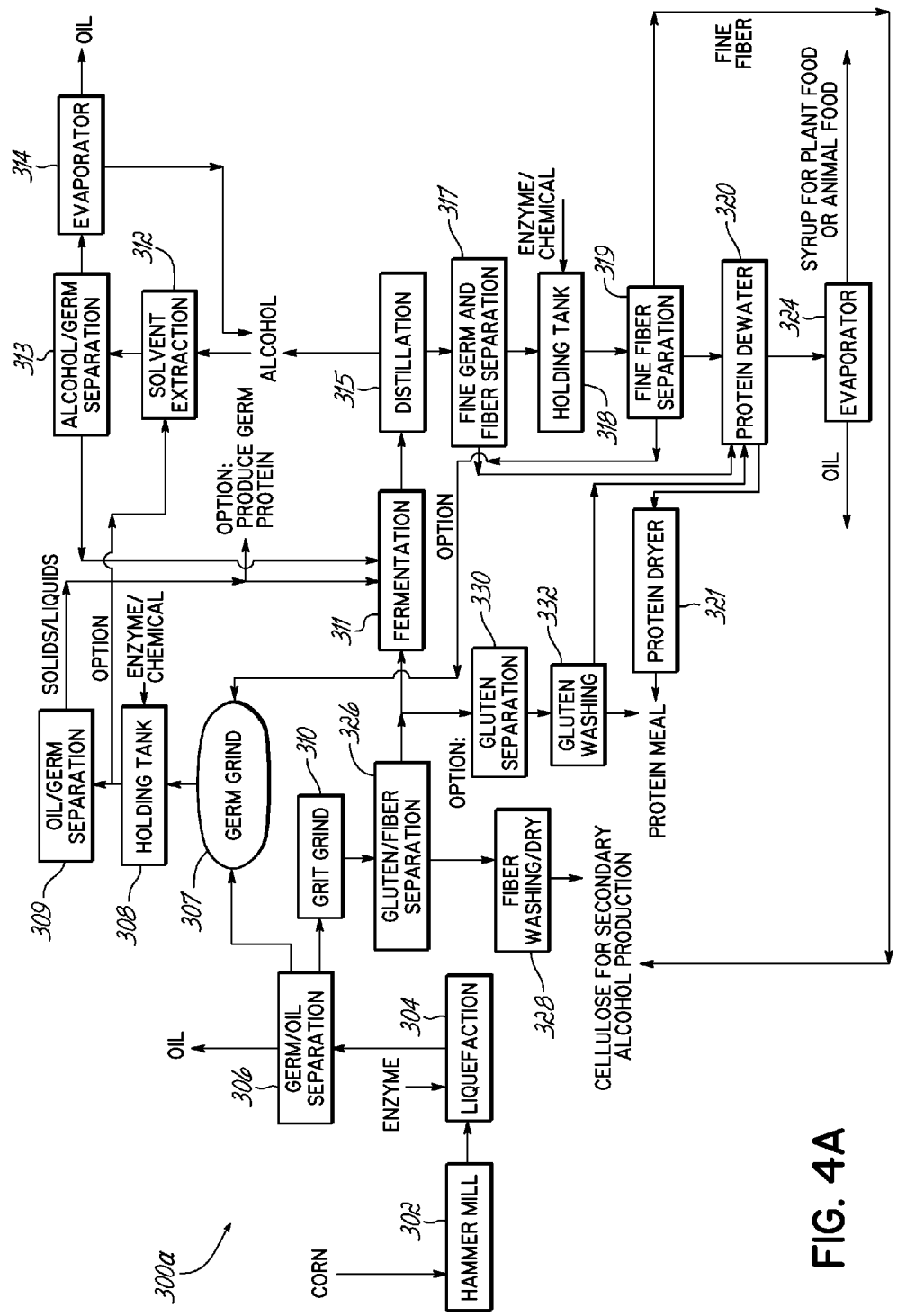
FIG. 4A is a flow diagram of a variation of the system and method of FIG. 4.

With reference now to FIG. 4A, this figure depicts a flow diagram of a variation of the system and method 300 of FIG. 4. In this system and method 300a, the cellulosic material and the gluten (protein) meal can be removed prior to fermentation 311. Recovery of the gluten meal before fermentation 311 can cut down on xanthophyll loss during fermentation 311 and subsequent distillation and protein recovery steps 315, 320. In addition, larger size pericarp particles, such as from about 1 mm to about 4 mm, can plug heat exchangers used during fermentation 311. So removal of the pericarp before fermentation 311 can avoid these plugging problems and can increase fermentation capacity by about 15% over conventional processes.

As shown in FIG. 4A, after the germ/oil separation step 306, the liquefied starch solution along with the grit, fiber, and protein is subjected to the grinding step 310 followed by a gluten/fiber separation step 326 using a screen device, such as a filtration centrifuge, to remove the fiber therefrom. The screen openings normally will be about 500 microns to capture amounts of tipcap, pericarp, as well as fine fiber, but can range from about 300 micron to about 700 micron. The separated fiber is washed and optionally dried, as represented by numeral 328, to produce a cellulose for secondary alcohol production. The resulting cellulosic material, which includes pericarp and tipcap and has up to about 15% protein, up to about 5% oil, and up to about 4% starch, can be sent to a secondary alcohol system as feed stock without any further treatment.

The protein portion from the liquefied starch solution centrate after gluten/fiber separation step 326 can optionally be separated out, as represented by numeral 330, using a centrifuge, such as a disc decanter, or a nozzle centrifuge/decanter combination. The separated protein is further subjected to a washing step 332 and can yield a high value protein meal having a desirable percentage of xanthopyll, i.e., from about 100 mg/Lb to about 200 mg/Lb, which can be further combined with residual protein that is separated out downstream as discussed in detail further below. Otherwise, the liquefied starch solution centrate portion meets up with the fine germ particles at the fermentation step 311. As another option, the fine germ particles from the oil/germ separation step 309 can be further processed to separate out and produce germ protein prior to joining up with the liquefied starch solution at the fermentation step 311.

The remainder of the process is generally the same as that of FIG. 4, with the exception that the gluten meal and fiber have been recovered on the front end of the process prior to fermentation 311. In particular, where the fiber was previously separated from the protein, fine germ particles and fine fiber, there is now no such separation step 316 (FIG. 4). Instead, fine fiber and fine germ having a size larger than 50 microns are separated from residual protein (gluten) at fine germ and fiber separation step 317. Here, the fine germ and fine fiber are separated using a fine screen device, such as paddle screen or pressure screen with a screen size of about 45 micron.

The fine germ and fine fiber are transported to a fine germ/fine fiber holding tank 318 whereat the pH of the fine germ/fiber in the tank can be adjusted to about 8 to about 10.5 (or about 8 to about 9.5), such as by the addition of chemicals, e.g., sodium hydroxide, lime, sodium carbonate, trisodium phosphate, or the like to help release additional oil from the germ. Also, cell wall breaking enzymes, e.g., protease and the like, and/or chemicals, e.g., sodium sulfite and the like, may be added here to help release additional oil from the germ. The germ and fiber mixture is next subjected to a fine fiber separation step 319 whereat the fine fiber is separated from the fine germ by a decanter, for example. The fine fiber then can be combined with the separated fiber that has been washed and optionally dried, as represented by numeral 328, for producing the cellulose for secondary alcohol production. In one example, the fine fiber includes less than 15% protein and 4% oil.

The centrate from the fine germ and fiber separation step 317, the overflow from the fine fiber separation step 319, and the overflow from the optional front end gluten washing step 332 is joined up at protein recovery/dewatering step 320, which uses, for example, a decanter, a nozzle centrifuge, or a disc decanter to recover the fine germ and protein (as well as spent yeast). Alternatively, the overflow from the fine fiber separation step 319 instead may be optionally dewatered using, for example, a decanter, a nozzle centrifuge, or a disc decanter and sent back to germ grind step 307 to extract more oil. The components from the recovery/dewatering step 320 are sent to the dryer 321 and combined with the optionally separated gluten from the front end to yield a gluten/germ/yeast mix (protein meal) having about 60% gluten and about 40% germ/yeast. The overflow from the protein dewatering step 320 goes to the evaporator 324 to separate any oil therefrom and to produce the high concentrated syrup (more than 65% DS), which again can be used, amongst other things, as (a) nutrition for secondary alcohol production, (b) animal feed stock, (c) plant food, (d) and/or anaerobic digestion to produce biogas.

With reference now to FIG. 5, this figure depicts a flow diagram of another embodiment of a system and method 400 for separating high value by-products from grains used for alcohol production. This system and method 400, which generally corresponds to a dry grind ethanol production system and process, separates various by-products to yield, for example, a low protein (less than 20%)/low oil (less than 8%) DDGS, such as for cows or pigs and high value oil. To that end, in this specific process and method 400, the corn is first subjected to a hammer mill 402, for example, which can be used to grind the corn to particle sizes less than about 7/64 inch assisting in the release of oil therefrom. In one example, the particle size is from 50 microns to 3 mm. The grinding helps break up the bonds between the fiber, protein, starch, and germ. In another example, a germ fraction, such as from a dry fraction process, may replace the initially un-ground corn here. The ground corn is mixed with water and sent to a liquefaction step 404, which provides a liquefied starch solution having a density of about 1.05 to 1.15 grams/cc. At the liquefaction step 404, the starch begins converting to a liquefied starch solution. An enzyme(s), such as alpha amylase, can be added to the liquefaction step 404. Any suitable liquefaction apparatus, which is well known in the art, may be utilized here.

The stream from the liquefaction step 404 contains about 1 lb/Bu free oil and about 1.5 lb/Bu germ particle (size ranges from less about 50 micron to about 1 mm), 1 lb/Bu grit (size ranges from about 50 micron to about 1 mm), and 5 lb/Bu fiber (particle size ranges from about 50 micron to about 3 mm). This stream goes to a solid/liquid separation step 406, which uses any suitable filtration device, e.g., a pre-concentrator, paddle screen, pressure screen, fiber centrifuge, and the like, to separate the liquid from the solid material. The screen openings can range from about 50 micron to about 500 micron and will be selected to desirably separate the fiber, grit, and germ particles from the liquid, which primarily includes the liquefied starch solution with small amounts of oil, free protein (mainly gluten), and starch. In one example, the screen openings are about 50 micron.

The liquid portion can go to an oil/liquefied starch separation step 408 whereat the liquid portion is subjected to a centrifuge, such as a disc centrifuge, to separate the oil out before sending the liquefied starch solution to meet up with the treated solids portion prior to fermentation, which is discussed below. At oil/liquefied starch separation step 408, the liquefied starch solution is used as heavy media liquid to float the oil, which has a density of about 1.05 to 1.15 grams/cc. The oil that is recovered at this stage in the process has a much more desirable quality in terms of color and free fatty acid content (from about 2% to about 5%) as compared to oil that is recovered downstream, particularly oil recovered after fermentation. In particular, the color of the pre-fermentation recovered oil is lighter in color and lower in free fatty acid content. The oil yield can include 0.8 lb/Bu or greater. In one example, the oil yield is from about 0.8 to about 1.0 lb/Bu.

The separated solids portion from the solid/liquid separation step 406 is subjected to a size reduction step 410 using a grind mill, pin mill, or high pressure cooker step, for example, to further breakdown the bond between the fiber, starch, and protein. Various enzymes (and types thereof) such as glucoamylase, fungal, cellulose, cellobiose, protease, and the like also can be optionally added to enhance the separation. The treated solids portion from the size reduction step 410 and the liquefied starch solution from the oil/liquefied starch separation step 408 are then combined together. The liquefied starch solution, which now includes the fiber, grit, germ, and protein, is subjected to a fermentation step 412 followed by distillation 414. At the distillation tower, the fermented solution is separated from the stillage, which includes fiber, protein, and germ particles, to produce alcohol. The fiber can be separated from the germ particles and protein (gluten) at a fiber/protein separation step 416 by differences in particle sizes using a screen device, such as a filtration centrifuge, to remove the fiber therefrom. The screen openings normally will be about 500 microns to capture amounts of tipcap, pericarp, as well as fine fiber, but can range from about 300 micron to about 700 micron. The separated fiber is used to produce a low protein (less than 20%)/low oil (less than 8%) DDG.

If a lower protein and oil content in the fiber is needed or desired, the fiber may be sent to a holding tank (not shown), for example, whereat the pH of the separated fiber can be adjusted to about 8 to about 10.5 (or about 8 to about 9.5), such as by the addition of chemicals, e.g., sodium hydroxide, lime, sodium carbonate, trisodium phosphate, or the like to help release additional oil from the germ. Also, cell wall breaking enzymes, e.g., protease and the like, and/or chemicals, e.g., sodium sulfite and the like, may be added here to help release additional oil from the germ. In one example, the fiber can be held in the tank for about 1 hour at a temperature of about 140° F. to about 200° F. (or about 180° F. to about 200° F.). Thereafter, the fiber can be subjected to a grind step to release more oil and protein from the fiber. The fiber produced by these additional treatment steps can give a much lower oil (less than 2%) and lower protein (less than 10%) and can be used for secondary alcohol production.

The centrate from the fiber/protein separation step 416 goes to a protein recovery/dewatering step 418, which uses, for example, a decanter, a nozzle centrifuge, or a disc decanter to recover the fine germ and protein (as well as spent yeast). These components are sent to a dryer 420 to yield a high value gluten/germ/yeast mix (protein meal) having about 60% gluten and about 40% germ/yeast. This system and method 400 will produce a protein yield of 5.5 lb/Bu, with about 45% protein purity. Alternatively, prior to the protein recovery/dewatering step 418, the centrate from the fiber/protein separation step 416 instead may first be optionally sent to a germ/gluten separation step 422 whereat the germ is separated from the gluten using, for example, a paddle screen or pressure screen. The germ is sent back to germ grind step 410 to extract more oil. The gluten is sent on to protein recovery/dewatering step 418, then to the protein dryer 420.

The overflow from the protein dewatering step 418 goes to an evaporator 424 to separate any oil therefrom and to produce syrup, which can be mixed with the DDG and dried, as represented by numeral 426, to give the low protein (less than 20%)/low oil (less than 8%) DDGS, such as for cows or pigs, particularly dairy cows. The DDGS contains less than about 20% protein, less than about 8% oil, and less than 4% starch.

In addition, an optional centrifugation step (not shown) may be provided to recover the xanthophyll content in the emulsion layer of the recovered oils, both prior to and after fermentation 412, and mixed with the protein by-product prior to drying to increase the feed value. Sodium sulfite, sulfur dioxide, or the like may be added to the wet protein cake, for example, to maintain more than a 20 ppm sulfur dioxide level before the wet protein cake is sent to the protein dryer 420. The sulfur dioxide can prevent the xanthophylls from decomposing inside the protein dryer 420. The overflow from the centrifuge(s) can go back to the oil storage tanks. In addition, although not shown, it should be understood that the fiber, protein, fine germ, and fine fiber of the stillage from distillation may be treated in a manner as illustrated at the back end of the methods 300, 400 of FIGS. 3 and 4.

Figure 5A:
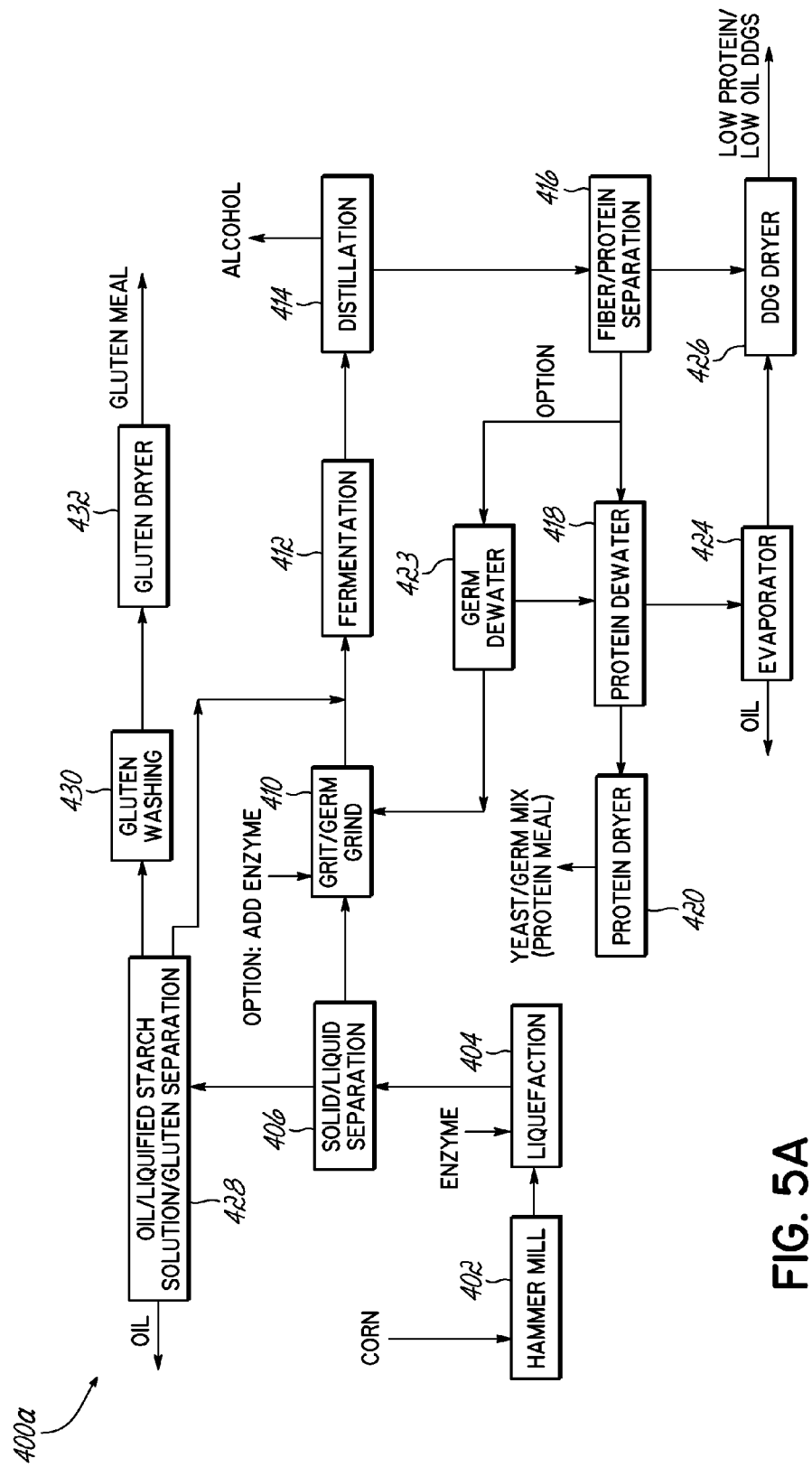
FIG. 5A is a flow diagram of a variation of the system and method of FIG. 5.
Figure 5B:
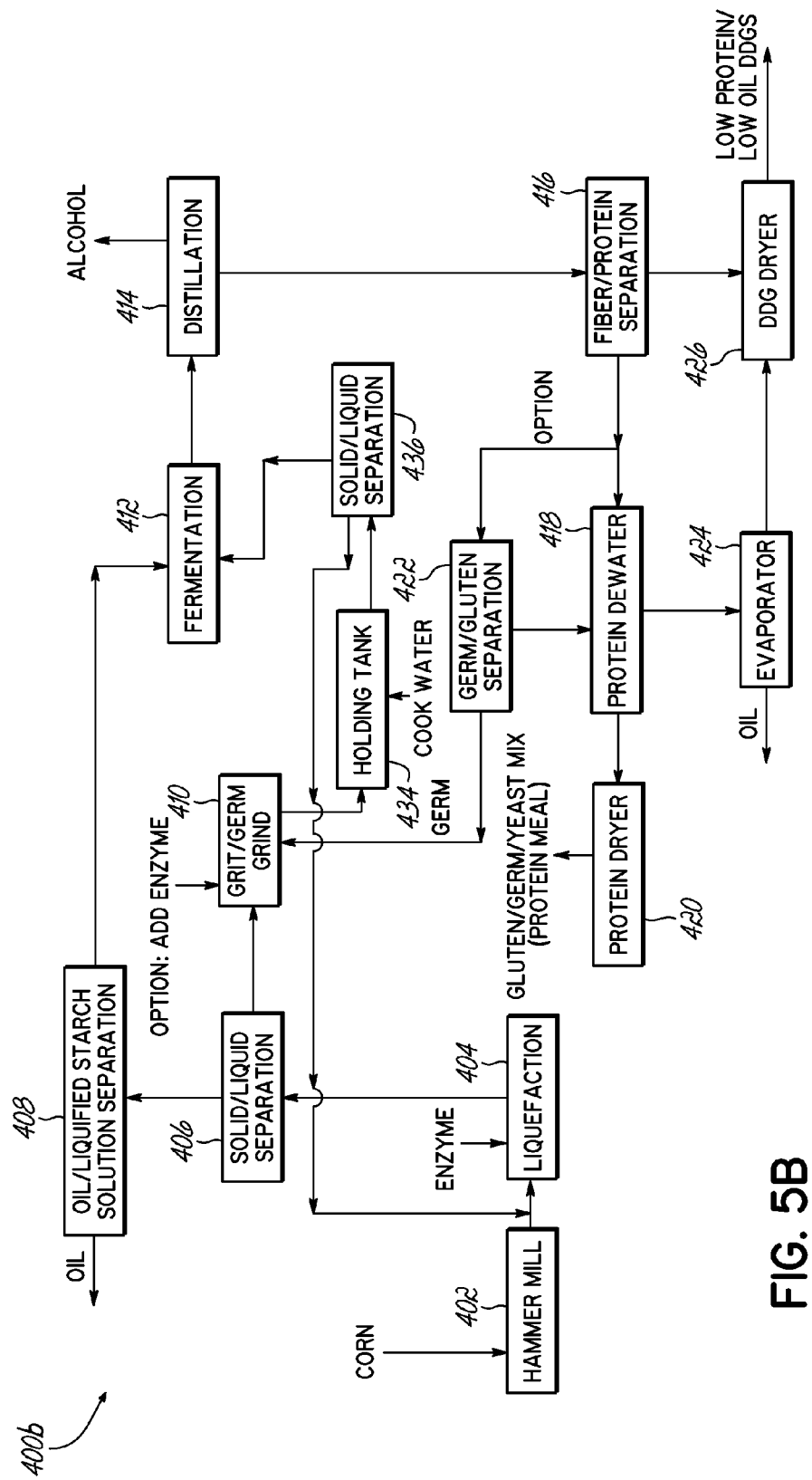
FIG. 5B is a flow diagram of another variation of the system and method of FIG. 5.

With reference now to FIG. 5A, this figure depicts a flow diagram of a variation of the system and method 400 of FIG. 5. In this system and method 400a, the gluten meal is removed prior to fermentation 412. Recovery of the gluten meal before fermentation 412 can cut down on xanthophyll loss during fermentation 412 and subsequent distillation and protein recovery steps 414, 418.

As shown in FIG. 5A, after the solid/liquid separation step 406, the liquid portion can go to an oil/liquefied starch solution/gluten separation step 428 whereat the liquid portion is subjected to a disc centrifuge or disc decanter centrifuge to individually separate the oil and the gluten from the liquefied starch solution, which is sent to meet up with the treated solids portion prior to fermentation 412. At the oil/liquefied starch solution/gluten separation step 428, the liquefied starch solution is used as heavy media liquid to float and separate the oil, which has a density of about 0.9 to 0.92 grams/cc. The gluten is discharged as a cake from separation step 428 and goes to a gluten washing step 430 followed by a gluten drying step 432 to yield a high value gluten meal having a desirable percentage of xanthopyll, i.e., from about 100 mg/Lb to about 200 mg/Lb.

The remainder of the process is generally the same as that of FIG. 5, with the exception that the gluten meal has been recovered on the front end of the process, prior to fermentation 412. In particular, the optional germ/gluten separation step 422 (FIG. 5) is now an optional germ dewatering step 423, which uses, for example, a paddle screen or pressure screen to recover the fine germ. The germ is sent back to germ grind step 410 to extract more oil. The centrate is sent on to protein recovery/dewatering step 418, then the recovered components sent to the protein dryer 420. The resulting gluten/germ/yeast mix (protein meal) includes a lower percentage of gluten. The overflow from the protein recovery/dewatering step 418 still makes its way to the evaporator 424 to separate any oil therefrom and to produce syrup, which can be mixed with the DDG and dried to give the low protein (less than 20%)/low oil (less than 8%) DDGS.

With reference now to FIG. 5B, this figure depicts a flow diagram of a variation of the system and method 400 of FIG. 5. In this system and method 400b, the treated solids portion from the size reduction step 410 is first sent to a holding tank 434 then a solid/liquid separation step 436 before being combined together with the liquefied starch solution from the oil/liquefied starch separation step 408 at fermentation step 412.

In particular, as shown in FIG. 5B, the treated solids portion is mixed with cook water at holding tank 434 whereat the bonds between fiber, starch, protein, and oil of the fine germ and fine fiber can be further broken down. In addition, the pH of the fine germ can be adjusted here to about 8 to about 10.5 (or about 8 to about 9.5), such as by the addition of chemicals, e.g., sodium hydroxide, lime, sodium carbonate, trisodium phosphate, or the like, to help release oil from the germ. Also, cell wall breaking enzymes, e.g., protease and the like, and/or chemicals, e.g., sodium sulfite and the like, may be added here to help release oil from the germ. In one example, the fine germ can be held in the tank for about 1 hour at a temperature of about 140° F. to about 200° F. (or about 180° F. to about 200° F.).

After the holding tank 434, the slurry is sent to solid/liquid separation step 436 whereat the solids and liquids are separated by using, for example, a paddle screen or pressure screen. The size of the openings in the screen is larger than those of the screens used at solid/liquid separation step 406. In one example, the openings can range from about 100 microns to 400 microns. In another example, the openings in the screen are about 250 microns. The liquid centrate, which includes fine germ particles and fine fiber particles smaller than the size of the screen openings, is returned to mix with the milled grains after the hammer mill 402 and prior to liquefaction step 404 to form a slurry and for further processing, such as to recover additional oil by-product. The solids portion from the solid/liquid separation step 436 and the liquefied starch solution from the oil/liquefied starch separation step 408 are then combined together and subjected to fermentation step 412 followed by distillation 414. The remainder of the process is generally the same as that of FIG. 5, including optionally sending the fine germ from gluten/separation step 422 back to germ grind step 410 to extract more oil, which will be further subjected to holding tank 434 and solid/liquid separation step 436. With this system and method 400b, the oil yield from the oil/liquefied starch solution separation step 408 is 1.0 lb/Bu or greater. In one example, the oil yield is from about 1.2 to about 1.4 lb/Bu. In addition, it should be understood that these additional steps 434 and 436 may be similarly implemented in the processes as shown in FIGS. 3-5A.

Accordingly, an improved system and method for separating high value by-products, such as oil, white fiber, and protein meal, from grains used for alcohol production, which is an improvement over typical processes and others, is provided that overcomes drawbacks of current systems and methods.

While the present invention has been illustrated by a description of various embodiments and while these embodiments have been described in considerable detail, it is not the intention of the applicant to restrict or in any way limit the scope of the appended claims to such detail. For example, although the various systems and methods described herein have focused on corn, virtually any type of grain, including, but not limited to, wheat, barley, sorghum, rye, rice, oats and the like, can be used. It is also contemplated that any byproduct, such as fiber protein from current corn wet mill processes or germ fractions and fiber fractions from current dry fractionation processes can be used. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method for front end separation of an oil by-product from grains used in an alcohol production process, the method comprising:
   grinding the grains into grain particles to release oil from the grains;
   mixing the grain particles with a liquid to form a slurry including starch, fiber, protein, germ, and the released oil defining free oil in the slurry;
   subjecting the slurry to liquefaction to provide a liquefied starch solution including sugars and the fiber, protein, germ, and free oil;
   separating solids including the fiber and germ from the liquefied starch solution including the free oil and sugars;
   thereafter and prior to fermentation, separating the free oil from the liquefied starch solution to yield the oil by-product; and
   after separating the free oil from the liquefied starch solution, rejoining the liquefied starch solution including the sugars with the separated solids, then subjecting the mixture to fermentation to produce alcohol.

2. The method of claim 1 wherein the oil yield is from about 0.8 to 1.0 lb/Bu.

3. The method of claim 1 wherein separating the free oil from the liquefied starch solution further comprises individually separating gluten and the free oil from the liquefied starch solution to yield the oil and a gluten by-product.

4. The method of claim 1 further comprising grinding the separated solids from the liquefied starch solution to produce fine fiber and fine germ, separating the fine fiber and fine germ from the ground solids prior to fermentation, and subjecting the fine fiber and fine germ to the liquefaction with the milled grains used for alcohol production to provide the liquefied starch solution including fiber, protein, germ, and free oil.

5. The method of claim 4 further comprising combining fine germ recovered after distillation with the separated solids including fiber and germ from the liquefied starch solution, and grinding the separated solids from the liquefied starch solution and the fine germ recovered after distillation to produce the fine fiber and fine germ.

6. The method of claim 1 wherein the alcohol is ethanol.

7. The method of claim 1 wherein the grains include at least one of corn, wheat, barley, sorghum, rye, rice, or oats.

* * * * *